(12) United States Patent
Buan et al.

(10) Patent No.: US 8,945,074 B2
(45) Date of Patent: Feb. 3, 2015

(54) DEVICE WITH CONTROLLER AND PUMP MODULES FOR PROVIDING NEGATIVE PRESSURE FOR WOUND THERAPY

(75) Inventors: John Buan, Maple Grove, MN (US); Alan Carlson, St. Paul, MN (US); Daniel Gelfman, Golden Valley, MN (US)

(73) Assignee: Kalypto Medical, Inc., Mendota Heights, MN (US)

( * ) Notice: Subject to any disclaimer, the term of this patent is extended or adjusted under 35 U.S.C. 154(b) by 85 days.

(21) Appl. No.: 13/247,435

(22) Filed: Sep. 28, 2011

(65) Prior Publication Data

US 2012/0302975 A1     Nov. 29, 2012

Related U.S. Application Data

(60) Provisional application No. 61/489,299, filed on May 24, 2011.

(51) Int. Cl.
*A61M 1/00* (2006.01)
*A61M 13/00* (2006.01)

(52) U.S. Cl.
CPC ........... *A61M 1/0031* (2013.01); *A61M 1/0025* (2014.02); *A61M 1/0088* (2013.01); *A61M 2205/583* (2013.01); *Y10S 604/902* (2013.01)
USPC ............. 604/318; 604/35; 604/305; 604/306; 604/307; 604/308; 604/317; 604/319; 604/320; 604/321; 604/322; 604/323; 604/540; 604/541; 604/542; 604/543; 604/544; 604/902; 606/131

(58) Field of Classification Search
CPC ....... A61M 1/00; A61M 39/02; A61M 27/00; A61F 13/00; A61B 17/50
USPC ........... 604/317–323, 35, 305–308, 540–544, 604/902; 606/131
See application file for complete search history.

(56) References Cited

U.S. PATENT DOCUMENTS

| | | | |
|---|---|---|---|
| 695,270 A | 3/1902 | Beringer |
| 1,480,562 A | 1/1924 | Mock |
| (Continued) | | |

FOREIGN PATENT DOCUMENTS

| | | |
|---|---|---|
| CA | 2198243 A1 | 2/1996 |
| CA | 2367460 A1 | 10/2000 |
| (Continued) | | |

OTHER PUBLICATIONS

U.S. Appl. No. 60/559,727, filed Apr. 5, 2004, Richard Scott Weston.

(Continued)

*Primary Examiner* — Tatyana Zalukaeva
*Assistant Examiner* — Ilya Treyger
(74) *Attorney, Agent, or Firm* — Knobbe Martens Olson & Bear, LLP

(57) ABSTRACT

A device for use with a negative pressure bandage for supply negative pressure. The device includes a pump module and a controller module. The pump module contains a power source and a pump. The pump module is removably contained in the controller module. The pump module and controller module can be connected with a connector that provides both a physical and pneumatic connection. The controller module may include one of more visual indicators for allowing the status of the device to be observed at a distance.

18 Claims, 3 Drawing Sheets

(56) References Cited

U.S. PATENT DOCUMENTS

| | | |
|---|---|---|
| 2,280,915 A | 4/1942 | Johnson |
| 2,367,690 A | 1/1945 | Purdy |
| 2,568,933 A | 9/1951 | Robbins |
| 2,632,443 A | 3/1953 | Lesher |
| 2,682,873 A | 7/1954 | Evans et al. |
| 3,367,332 A | 2/1968 | Groves |
| 3,486,504 A | 12/1969 | Austin et al. |
| 3,572,340 A | 3/1971 | Lloyd et al. |
| 3,610,238 A | 10/1971 | Rich et al. |
| 3,874,387 A | 4/1975 | Barbieri |
| 3,993,080 A | 11/1976 | Loseff |
| RE29,319 E | 7/1977 | Nordby et al. |
| 4,102,342 A | 7/1978 | Akiyama et al. |
| 4,112,947 A | 9/1978 | Nehring |
| 4,136,696 A | 1/1979 | Nehring |
| 4,184,510 A | 1/1980 | Murry et al. |
| 4,217,894 A | 8/1980 | Franetzki |
| 4,219,019 A | 8/1980 | Coates |
| 4,224,945 A | 9/1980 | Cohen |
| 4,250,882 A | 2/1981 | Adair |
| 4,316,466 A | 2/1982 | Babb |
| 4,382,441 A | 5/1983 | Svedman |
| 4,465,485 A | 8/1984 | Kashmer et al. |
| 4,468,227 A | 8/1984 | Jensen |
| 4,525,166 A | 6/1985 | Leclerc |
| 4,534,356 A | 8/1985 | Papadakis |
| 4,551,141 A | 11/1985 | McNeil |
| 4,573,965 A | 3/1986 | Russo |
| 4,608,041 A | 8/1986 | Nielsen |
| 4,655,766 A | 4/1987 | Theeuwes et al. |
| 4,681,562 A | 7/1987 | Beck et al. |
| 4,710,165 A | 12/1987 | McNeil et al. |
| 4,778,446 A | 10/1988 | Jensen |
| 4,778,456 A | 10/1988 | Lokken |
| 4,792,328 A | 12/1988 | Beck et al. |
| 4,795,435 A | 1/1989 | Steer |
| 4,820,284 A | 4/1989 | Hauri |
| 4,921,488 A | 5/1990 | Maitz et al. |
| 4,936,834 A | 6/1990 | Beck et al. |
| 4,950,483 A | 8/1990 | Ksander et al. |
| 4,969,880 A | 11/1990 | Zamierowski |
| 4,972,829 A | 11/1990 | Knerr |
| 4,979,944 A | 12/1990 | Luzsicza |
| 4,994,022 A | 2/1991 | Steffler et al. |
| 5,055,198 A | 10/1991 | Shettigar |
| 5,056,510 A | 10/1991 | Gilman |
| 5,073,172 A | 12/1991 | Fell |
| 5,100,396 A | 3/1992 | Zamierowski |
| 5,149,331 A | 9/1992 | Ferdman et al. |
| 5,152,757 A | 10/1992 | Eriksson |
| 5,167,613 A | 12/1992 | Karami et al. |
| 5,176,663 A | 1/1993 | Svedman et al. |
| 5,215,519 A | 6/1993 | Shettigar |
| 5,261,893 A | 11/1993 | Zamierowski |
| 5,266,928 A | 11/1993 | Johnson |
| 5,279,608 A | 1/1994 | Cherif Cheikh |
| 5,328,614 A | 7/1994 | Matsumura |
| 5,358,494 A | 10/1994 | Svedman |
| 5,380,280 A | 1/1995 | Peterson |
| 5,437,651 A | 8/1995 | Todd et al. |
| 5,445,604 A | 8/1995 | Lang |
| 5,489,280 A | 2/1996 | Russell |
| 5,498,338 A | 3/1996 | Kruger et al. |
| 5,527,293 A | 6/1996 | Zamierowski |
| 5,549,584 A | 8/1996 | Gross |
| 5,636,643 A | 6/1997 | Argenta et al. |
| 5,643,189 A | 7/1997 | Masini |
| 5,645,081 A | 7/1997 | Argenta et al. |
| 5,678,564 A | 10/1997 | Lawrence et al. |
| 5,733,337 A | 3/1998 | Carr et al. |
| 5,759,570 A | 6/1998 | Arnold |
| 5,785,688 A | 7/1998 | Joshi et al. |
| 5,830,496 A | 11/1998 | Freeman |
| 5,833,646 A | 11/1998 | Masini |
| 5,843,011 A | 12/1998 | Lucas |
| 5,857,502 A | 1/1999 | Buchalter |
| 5,868,933 A | 2/1999 | Patrick et al. |
| 5,876,611 A | 3/1999 | Shettigar |
| 5,964,723 A | 10/1999 | Augustine |
| 6,071,267 A | 6/2000 | Zamierowski |
| 6,103,951 A | 8/2000 | Freeman |
| 6,110,197 A | 8/2000 | Augustine et al. |
| 6,135,116 A | 10/2000 | Vogel et al. |
| D434,150 S | 11/2000 | Tumey et al. |
| 6,142,982 A | 11/2000 | Hunt et al. |
| 6,168,800 B1 | 1/2001 | Dobos et al. |
| 6,176,307 B1 | 1/2001 | Danos et al. |
| 6,225,523 B1 | 5/2001 | Masini |
| 6,254,567 B1 | 7/2001 | Treu et al. |
| 6,255,552 B1 | 7/2001 | Cummings et al. |
| 6,261,283 B1 | 7/2001 | Morgan et al. |
| 6,287,521 B1 | 9/2001 | Quay et al. |
| 6,345,623 B1 | 2/2002 | Heaton et al. |
| 6,398,767 B1 | 6/2002 | Fleischmann |
| 6,402,724 B1 | 6/2002 | Smith et al. |
| 6,450,773 B1 | 9/2002 | Upton |
| 6,458,109 B1 | 10/2002 | Henley et al. |
| 6,465,708 B1 | 10/2002 | Augustine |
| 6,471,685 B1 | 10/2002 | Johnson |
| 6,471,982 B1 | 10/2002 | Lydon et al. |
| 6,482,491 B1 | 11/2002 | Samuelsen et al. |
| 6,491,684 B1 | 12/2002 | Joshi et al. |
| 6,553,998 B2 | 4/2003 | Heaton et al. |
| 6,599,262 B1 | 7/2003 | Masini |
| 6,648,862 B2 | 11/2003 | Watson |
| 6,673,028 B1 | 1/2004 | Argenta et al. |
| 6,676,610 B2 | 1/2004 | Morton et al. |
| 6,685,681 B2 | 2/2004 | Lockwood et al. |
| 6,695,823 B1 | 2/2004 | Lina et al. |
| 6,695,824 B2 | 2/2004 | Howard et al. |
| 6,752,794 B2 | 6/2004 | Lockwood et al. |
| 6,755,807 B2 | 6/2004 | Risk, Jr. et al. |
| 6,764,462 B2 | 7/2004 | Risk, Jr. et al. |
| 6,767,334 B1 | 7/2004 | Randolph |
| 6,814,079 B2 | 11/2004 | Heaton et al. |
| 6,824,533 B2 | 11/2004 | Risk, Jr. et al. |
| 6,855,135 B2 | 2/2005 | Lockwood et al. |
| 6,856,821 B2 | 2/2005 | Johnson |
| 6,936,037 B2 | 8/2005 | Bubb |
| 6,951,553 B2 | 10/2005 | Bubb et al. |
| 6,977,323 B1 | 12/2005 | Swenson |
| 6,979,324 B2 | 12/2005 | Bybordi et al. |
| 6,994,702 B1 | 2/2006 | Johnson |
| 7,004,915 B2 | 2/2006 | Boynton et al. |
| 7,022,113 B2 | 4/2006 | Lockwood et al. |
| 7,067,709 B2 | 6/2006 | Murata et al. |
| 7,070,584 B2 | 7/2006 | Johnson et al. |
| 7,077,832 B2 | 7/2006 | Fleischmann |
| 7,087,806 B2 | 8/2006 | Scheinberg et al. |
| 7,108,683 B2 | 9/2006 | Zamierowski |
| 7,118,545 B2 | 10/2006 | Boyde |
| 7,128,735 B2 | 10/2006 | Weston |
| 7,195,624 B2 | 3/2007 | Lockwood |
| 7,214,202 B1 | 5/2007 | Vogel et al. |
| 7,216,651 B2 | 5/2007 | Argenta et al. |
| 7,361,184 B2 | 4/2008 | Joshi |
| 7,381,859 B2 | 6/2008 | Hunt et al. |
| 7,438,705 B2 | 10/2008 | Karpowicz et al. |
| 7,494,482 B2 | 2/2009 | Orgill et al. |
| 7,503,910 B2 | 3/2009 | Adahan |
| 7,524,315 B2 | 4/2009 | Blott et al. |
| 7,534,240 B1 | 5/2009 | Johnson |
| 7,534,927 B2 | 5/2009 | Lockwood |
| 7,569,742 B2 | 8/2009 | Haggstrom et al. |
| 7,611,500 B1 | 11/2009 | Lina et al. |
| 7,612,247 B2 | 11/2009 | Oyaski |
| 7,615,036 B2 | 11/2009 | Joshi et al. |
| 7,645,253 B2 | 1/2010 | Gura et al. |
| 7,645,269 B2 | 1/2010 | Zamierowski |
| 7,678,090 B2 | 3/2010 | Risk, Jr. |
| 7,699,823 B2 | 4/2010 | Haggstrom et al. |
| 7,699,830 B2 | 4/2010 | Martin |
| 7,708,724 B2 | 5/2010 | Weston |
| 7,717,313 B2 | 5/2010 | Criscuolo et al. |

(56) References Cited

U.S. PATENT DOCUMENTS

| | | |
|---|---|---|
| 7,753,894 B2 | 7/2010 | Blott et al. |
| 7,759,537 B2 | 7/2010 | Bishop et al. |
| 7,759,538 B2 | 7/2010 | Fleischmann |
| 7,759,539 B2 | 7/2010 | Shaw et al. |
| 7,763,000 B2 | 7/2010 | Risk, Jr. |
| 7,775,998 B2 | 8/2010 | Riesinger |
| 7,776,028 B2 | 8/2010 | Miller et al. |
| 7,779,625 B2 | 8/2010 | Joshi et al. |
| 7,790,945 B1 | 9/2010 | Watson, Jr. |
| 7,790,946 B2 | 9/2010 | Mulligan |
| 7,794,438 B2 | 9/2010 | Henley et al. |
| 7,794,450 B2 | 9/2010 | Blott et al. |
| 7,811,269 B2 | 10/2010 | Boynton |
| 7,815,616 B2 | 10/2010 | Boehringer et al. |
| 7,825,289 B2 | 11/2010 | Vess |
| 7,828,782 B2 | 11/2010 | Suzuki |
| 7,838,717 B2 | 11/2010 | Haggstrom et al. |
| 7,846,141 B2 | 12/2010 | Weston |
| 7,862,339 B2 | 1/2011 | Mulligan |
| 7,883,494 B2 | 2/2011 | Martin |
| 7,909,805 B2 | 3/2011 | Weston |
| 7,959,624 B2 | 6/2011 | Riesinger |
| 7,964,766 B2 | 6/2011 | Blott et al. |
| 7,976,519 B2 | 7/2011 | Bubb et al. |
| 7,998,125 B2 | 8/2011 | Weston |
| 8,062,272 B2 | 11/2011 | Weston |
| 8,062,273 B2 | 11/2011 | Weston |
| 8,080,702 B2 | 12/2011 | Blott et al. |
| 8,100,887 B2 | 1/2012 | Weston |
| 8,105,295 B2 | 1/2012 | Blott et al. |
| 8,118,794 B2 | 2/2012 | Weston |
| 8,128,615 B2 | 3/2012 | Blott |
| 8,152,785 B2 | 4/2012 | Vitaris |
| 8,162,907 B2 | 4/2012 | Heagle |
| 8,162,909 B2 | 4/2012 | Blott et al. |
| 8,167,869 B2 | 5/2012 | Wudyka |
| 8,235,955 B2 | 8/2012 | Blott et al. |
| 8,282,611 B2 | 10/2012 | Weston |
| 8,294,586 B2 | 10/2012 | Pidgeon et al. |
| 8,308,714 B2 | 11/2012 | Weston et al. |
| 8,323,264 B2 | 12/2012 | Weston et al. |
| 8,353,857 B2 | 1/2013 | Rosenberg |
| 8,366,692 B2 | 2/2013 | Weston |
| 8,377,016 B2 | 2/2013 | Argenta et al. |
| 8,444,392 B2 | 5/2013 | Turner et al. |
| 8,494,349 B2 | 7/2013 | Gordon |
| 8,617,129 B2 | 12/2013 | Hartwell |
| 8,663,198 B2 | 3/2014 | Buan et al. |
| 8,663,200 B2 | 3/2014 | Weston et al. |
| 2001/0016205 A1 | 8/2001 | Shimizu |
| 2001/0029956 A1 | 10/2001 | Argenta |
| 2001/0034499 A1 | 10/2001 | Sessions et al. |
| 2002/0065494 A1 | 5/2002 | Lockwood et al. |
| 2002/0068913 A1 | 6/2002 | Fleischmann |
| 2002/0115952 A1 | 8/2002 | Tumey |
| 2002/0120185 A1 | 8/2002 | Johnson |
| 2002/0143286 A1 | 10/2002 | Tumey |
| 2002/0150720 A1 | 10/2002 | Howard et al. |
| 2002/0161346 A1 | 10/2002 | Lockwood et al. |
| 2002/0183702 A1 | 12/2002 | Henley et al. |
| 2002/0198503 A1 | 12/2002 | Risk et al. |
| 2002/0198504 A1 | 12/2002 | Risk et al. |
| 2003/0014022 A1 | 1/2003 | Lockwood et al. |
| 2003/0014025 A1 | 1/2003 | Allen et al. |
| 2003/0021775 A1 | 1/2003 | Freeman |
| 2003/0040687 A1 | 2/2003 | Boynton et al. |
| 2003/0050594 A1 | 3/2003 | Zamierowski |
| 2003/0088202 A1 | 5/2003 | Gilman |
| 2003/0097086 A1 | 5/2003 | Gura |
| 2003/0108587 A1 | 6/2003 | Orgill et al. |
| 2003/0125649 A1 | 7/2003 | McIntosh et al. |
| 2003/0144619 A1 | 7/2003 | Augustine |
| 2003/0171675 A1 | 9/2003 | Rosenberg |
| 2003/0175798 A1 | 9/2003 | Raees et al. |
| 2003/0208149 A1 | 11/2003 | Coffey |
| 2003/0212357 A1 | 11/2003 | Pace |
| 2003/0212431 A1 | 11/2003 | Brady et al. |
| 2003/0225347 A1 | 12/2003 | Argenta et al. |
| 2004/0019342 A1 | 1/2004 | Nagasuna et al. |
| 2004/0030304 A1 | 2/2004 | Hunt et al. |
| 2004/0039391 A1 | 2/2004 | Argenta et al. |
| 2004/0039415 A1 | 2/2004 | Zamierowski |
| 2004/0054338 A1 | 3/2004 | Bybordi et al. |
| 2004/0064132 A1 | 4/2004 | Boehringer et al. |
| 2004/0122434 A1 | 6/2004 | Argenta et al. |
| 2004/0127834 A1 | 7/2004 | Sigurjonsson et al. |
| 2004/0127862 A1 | 7/2004 | Bubb et al. |
| 2004/0127863 A1 | 7/2004 | Bubb et al. |
| 2004/0167482 A1 | 8/2004 | Watson |
| 2004/0225208 A1 | 11/2004 | Johnson |
| 2004/0241214 A1 | 12/2004 | Kirkwood et al. |
| 2004/0249353 A1 | 12/2004 | Risk, Jr. et al. |
| 2005/0004534 A1 | 1/2005 | Lockwood et al. |
| 2005/0010153 A1 | 1/2005 | Lockwood et al. |
| 2005/0020955 A1 | 1/2005 | Sanders et al. |
| 2005/0028828 A1 | 2/2005 | Heaton et al. |
| 2005/0033214 A1 | 2/2005 | Cantor |
| 2005/0058694 A1 | 3/2005 | Nielsen |
| 2005/0070835 A1 | 3/2005 | Joshi |
| 2005/0080372 A1 | 4/2005 | Nielsen et al. |
| 2005/0090787 A1 | 4/2005 | Risk, Jr. et al. |
| 2005/0148913 A1 | 7/2005 | Weston |
| 2005/0222527 A1 | 10/2005 | Miller et al. |
| 2005/0261643 A1 | 11/2005 | Bybordi et al. |
| 2006/0015087 A1 | 1/2006 | Risk, Jr. et al. |
| 2006/0025727 A1 | 2/2006 | Boehringer et al. |
| 2006/0029650 A1 | 2/2006 | Coffey |
| 2006/0041247 A1 | 2/2006 | Petrosenko et al. |
| 2006/0069365 A1 | 3/2006 | Sperl et al. |
| 2006/0079852 A1 | 4/2006 | Bubb et al. |
| 2006/0100586 A1 | 5/2006 | Karpowicz et al. |
| 2006/0100594 A1 | 5/2006 | Adams et al. |
| 2006/0116620 A1 | 6/2006 | Oyaski |
| 2006/0129137 A1 | 6/2006 | Lockwood |
| 2006/0149170 A1 | 7/2006 | Boynton et al. |
| 2007/0005028 A1 | 1/2007 | Risk, Jr. |
| 2007/0010797 A1 | 1/2007 | Nishtala et al. |
| 2007/0038172 A1 | 2/2007 | Zamierowski |
| 2007/0055209 A1 | 3/2007 | Patel et al. |
| 2007/0118096 A1 | 5/2007 | Smith et al. |
| 2007/0141128 A1 | 6/2007 | Blott et al. |
| 2007/0167884 A1 | 7/2007 | Mangrum et al. |
| 2007/0179460 A1 | 8/2007 | Adahan |
| 2007/0185426 A1 | 8/2007 | Ambrosio et al. |
| 2007/0185463 A1 | 8/2007 | Mulligan |
| 2007/0219532 A1 | 9/2007 | Karpowicz et al. |
| 2007/0239139 A1 | 10/2007 | Weston |
| 2007/0265585 A1 | 11/2007 | Joshi et al. |
| 2007/0265586 A1 | 11/2007 | Joshi et al. |
| 2008/0004549 A1 | 1/2008 | Anderson et al. |
| 2008/0004559 A1 | 1/2008 | Riesinger |
| 2008/0039759 A1 | 2/2008 | Holm et al. |
| 2008/0077091 A1 | 3/2008 | Mulligan |
| 2008/0082059 A1 | 4/2008 | Fink et al. |
| 2008/0108977 A1 | 5/2008 | Heaton et al. |
| 2008/0119802 A1 | 5/2008 | Riesinger |
| 2008/0167593 A1 | 7/2008 | Fleischmann |
| 2008/0183119 A1 | 7/2008 | Joshi |
| 2008/0188820 A1 | 8/2008 | Joshi |
| 2008/0208147 A1 | 8/2008 | Argenta et al. |
| 2008/0223378 A1 | 9/2008 | Henderson et al. |
| 2008/0306407 A1 | 12/2008 | Taylor |
| 2008/0306456 A1 | 12/2008 | Riesinger |
| 2009/0005746 A1 | 1/2009 | Nielsen et al. |
| 2009/0036873 A1 | 2/2009 | Nielsen et al. |
| 2009/0054855 A1 | 2/2009 | Blott et al. |
| 2009/0054856 A1 | 2/2009 | Mormino et al. |
| 2009/0069759 A1 | 3/2009 | Blott et al. |
| 2009/0105670 A1 | 4/2009 | Bentley et al. |
| 2009/0125004 A1 | 5/2009 | Shen et al. |
| 2009/0131888 A1 | 5/2009 | Joshi |
| 2009/0177135 A1 | 7/2009 | Rogers et al. |
| 2009/0192499 A1 | 7/2009 | Weston et al. |
| 2009/0198201 A1 | 8/2009 | Adahan |

(56) References Cited

U.S. PATENT DOCUMENTS

| | | |
|---|---|---|
| 2009/0216170 A1 | 8/2009 | Robinson et al. |
| 2009/0221977 A1 | 9/2009 | Blott et al. |
| 2009/0227968 A1 | 9/2009 | Vess |
| 2009/0227969 A1 | 9/2009 | Jaeb et al. |
| 2009/0234306 A1 | 9/2009 | Vitaris |
| 2009/0234307 A1 | 9/2009 | Vitaris |
| 2009/0234309 A1 | 9/2009 | Vitaris et al. |
| 2009/0240185 A1 | 9/2009 | Jaeb et al. |
| 2009/0240218 A1 | 9/2009 | Braga et al. |
| 2009/0254053 A1 | 10/2009 | Svensby et al. |
| 2009/0254054 A1 | 10/2009 | Blott et al. |
| 2009/0264837 A1 | 10/2009 | Adahan |
| 2009/0270820 A1 | 10/2009 | Johnson et al. |
| 2009/0299251 A1 | 12/2009 | Buan |
| 2009/0299255 A1 | 12/2009 | Kazala, Jr. et al. |
| 2009/0299256 A1 | 12/2009 | Barta et al. |
| 2009/0299257 A1 | 12/2009 | Long et al. |
| 2009/0299306 A1 | 12/2009 | Buan |
| 2009/0299307 A1 | 12/2009 | Barta et al. |
| 2009/0299341 A1 | 12/2009 | Kazala, Jr. et al. |
| 2009/0299342 A1 | 12/2009 | Cavanaugh, II et al. |
| 2009/0306580 A1 | 12/2009 | Blott et al. |
| 2009/0312723 A1 | 12/2009 | Blott et al. |
| 2009/0312728 A1 | 12/2009 | Randolph et al. |
| 2009/0326487 A1 | 12/2009 | Vitaris |
| 2010/0010477 A1 | 1/2010 | Augustine et al. |
| 2010/0036334 A1 | 2/2010 | Heagle et al. |
| 2010/0036367 A1 | 2/2010 | Krohn |
| 2010/0042074 A1 | 2/2010 | Weston et al. |
| 2010/0063483 A1 | 3/2010 | Adahan |
| 2010/0063484 A1 | 3/2010 | Heagle |
| 2010/0069858 A1 | 3/2010 | Olson |
| 2010/0069863 A1 | 3/2010 | Olson |
| 2010/0087767 A1 | 4/2010 | McNeil |
| 2010/0100063 A1 | 4/2010 | Joshi et al. |
| 2010/0100075 A1 | 4/2010 | Weston et al. |
| 2010/0106114 A1 | 4/2010 | Weston et al. |
| 2010/0121286 A1 | 5/2010 | Locke et al. |
| 2010/0122417 A1 | 5/2010 | Vrzalik et al. |
| 2010/0125258 A1 | 5/2010 | Coulthard et al. |
| 2010/0150991 A1 | 6/2010 | Bernstein |
| 2010/0160879 A1 | 6/2010 | Weston |
| 2010/0185163 A1 | 7/2010 | Heagle |
| 2010/0185165 A1 | 7/2010 | Middleton |
| 2010/0207768 A1 | 8/2010 | Pidgeon et al. |
| 2010/0249733 A9 | 9/2010 | Blott et al. |
| 2010/0262094 A1 | 10/2010 | Walton |
| 2010/0268198 A1 | 10/2010 | Buan et al. |
| 2010/0274207 A1 | 10/2010 | Weston |
| 2010/0278518 A1 | 11/2010 | Gordon |
| 2010/0280468 A1 | 11/2010 | Haggstrom et al. |
| 2010/0286489 A1 | 11/2010 | Hartwell |
| 2010/0286635 A1 | 11/2010 | Watson, Jr. |
| 2010/0286638 A1 | 11/2010 | Malhi |
| 2010/0298866 A1 | 11/2010 | Fischvogt |
| 2010/0305490 A1 | 12/2010 | Coulthard et al. |
| 2010/0305524 A1 | 12/2010 | Vess et al. |
| 2010/0318043 A1 | 12/2010 | Malhi et al. |
| 2010/0324510 A1 | 12/2010 | Andresen et al. |
| 2010/0324516 A1 | 12/2010 | Braga et al. |
| 2010/0331797 A1 | 12/2010 | Patel et al. |
| 2011/0004171 A1 | 1/2011 | Blott et al. |
| 2011/0004172 A1 | 1/2011 | Eckstein et al. |
| 2011/0009835 A1 | 1/2011 | Blott |
| 2011/0015593 A1 | 1/2011 | Svedman et al. |
| 2011/0028918 A1 | 2/2011 | Hartwell |
| 2011/0028921 A1 | 2/2011 | Hartwell et al. |
| 2011/0034892 A1 | 2/2011 | Buan |
| 2011/0046584 A1 | 2/2011 | Haggstrom et al. |
| 2011/0054421 A1 | 3/2011 | Hartwell |
| 2011/0054422 A1 | 3/2011 | Locke et al. |
| 2011/0054423 A1 | 3/2011 | Blott et al. |
| 2011/0071483 A1 | 3/2011 | Gordon et al. |
| 2011/0087176 A2 | 4/2011 | Blott |
| 2011/0087178 A2 | 4/2011 | Weston |
| 2011/0087180 A2 | 4/2011 | Weston |
| 2011/0092927 A1 | 4/2011 | Wilkes et al. |
| 2011/0092958 A1 | 4/2011 | Jacobs |
| 2011/0105963 A1 | 5/2011 | Hu et al. |
| 2011/0106030 A1 | 5/2011 | Scholz |
| 2011/0112492 A1 | 5/2011 | Bharti et al. |
| 2011/0118683 A1 | 5/2011 | Weston |
| 2011/0130712 A1 | 6/2011 | Topaz |
| 2011/0171543 A1 | 7/2011 | Hartwell |
| 2011/0172615 A2 | 7/2011 | Greener et al. |
| 2011/0230849 A1 | 9/2011 | Coulthard et al. |
| 2011/0251567 A1 | 10/2011 | Blott et al. |
| 2011/0275964 A1 | 11/2011 | Greener |
| 2011/0282309 A1 | 11/2011 | Adie et al. |
| 2012/0001762 A1 | 1/2012 | Turner et al. |
| 2012/0053538 A1 | 3/2012 | Blott et al. |
| 2012/0078539 A1 | 3/2012 | Vernon-Harcourt et al. |
| 2012/0109084 A1 | 5/2012 | Blott et al. |
| 2012/0130325 A1 | 5/2012 | Blott et al. |
| 2012/0136325 A1 | 5/2012 | Allen |
| 2012/0157942 A1 | 6/2012 | Weston |
| 2012/0165764 A1 | 6/2012 | Allen et al. |
| 2012/0302977 A1 | 11/2012 | Buan et al. |
| 2012/0302978 A1 | 11/2012 | Buan et al. |
| 2013/0018338 A1 | 1/2013 | Weston et al. |
| 2013/0110058 A1 | 5/2013 | Adie et al. |
| 2013/0150813 A1 | 6/2013 | Gordon |
| 2013/0267920 A1 | 10/2013 | Nicolini |
| 2013/0296816 A1 | 11/2013 | Greener |
| 2013/0331823 A1 | 12/2013 | Askem et al. |
| 2014/0088528 A1 | 3/2014 | Hartwell |
| 2014/0107599 A1 | 4/2014 | Fink et al. |

FOREIGN PATENT DOCUMENTS

| | | |
|---|---|---|
| CA | 2390513 A1 | 5/2001 |
| CA | 2121688 C | 7/2001 |
| CA | 2408305 A1 | 11/2001 |
| CA | 2458285 A1 | 3/2003 |
| CA | 2157772 C | 9/2003 |
| DE | 2809828 | 9/1978 |
| DE | 3 935 818 | 5/1991 |
| DE | 4 012 232 | 10/1991 |
| DE | 198 44 355 | 4/2000 |
| EP | 0 020 662 | 7/1984 |
| EP | 0 355 186 | 2/1990 |
| EP | 0 777 504 | 10/1998 |
| EP | 0 782 421 | 7/1999 |
| EP | 1 897 569 | 8/2002 |
| EP | 0 708 620 | 5/2003 |
| EP | 1 088 569 | 8/2003 |
| EP | 1 440 667 | 3/2006 |
| EP | 1 284 777 | 4/2006 |
| EP | 1 171 065 | 3/2007 |
| EP | 1 476 217 | 3/2008 |
| EP | 1 121 163 | 11/2008 |
| EP | 2098257 A1 | 9/2009 |
| FR | 1163907 | 10/1958 |
| GB | 114754 | 4/1918 |
| GB | 641061 | 8/1950 |
| GB | 1224009 A | 3/1971 |
| GB | 1549756 A | 8/1979 |
| GB | 2195255 A | 4/1988 |
| GB | 2378392 A | 2/2003 |
| GB | 2415908 A | 1/2006 |
| JP | 2003-165843 | 6/2003 |
| SU | 1251912 A1 | 4/1983 |
| WO | WO 84/01904 | 5/1984 |
| WO | WO 90/11795 | 10/1990 |
| WO | WO 91/00718 | 1/1991 |
| WO | WO 92/20299 | 11/1992 |
| WO | WO 96/05873 | 2/1996 |
| WO | WO 99/01173 | 1/1999 |
| WO | WO 00/07653 | 2/2000 |
| WO | WO 00/50143 A | 8/2000 |
| WO | WO 00/59424 | 10/2000 |
| WO | WO 01/19430 A1 | 3/2001 |
| WO | WO 01/34223 | 5/2001 |
| WO | WO 01/37922 | 5/2001 |

(56) References Cited

FOREIGN PATENT DOCUMENTS

| WO | WO 01/85248 | 11/2001 |
|---|---|---|
| WO | WO 01/93793 | 12/2001 |
| WO | WO 02/083046 A1 | 10/2002 |
| WO | WO 02/092783 | 11/2002 |
| WO | WO 03/045492 | 6/2003 |
| WO | WO 03/057307 | 7/2003 |
| WO | WO 03/092620 | 11/2003 |
| WO | WO 2004/024300 | 3/2004 |
| WO | WO 2004/037334 | 5/2004 |
| WO | WO 2005/025666 | 3/2005 |
| WO | WO 2005/051461 | 6/2005 |
| WO | WO 2005/070480 | 8/2005 |
| WO | WO 2005/082435 | 9/2005 |
| WO | WO 2007/024230 | 3/2007 |
| WO | WO 2007/030601 | 3/2007 |
| WO | WO2007024230 | 3/2007 |
| WO | WO 2009/066105 | 5/2009 |
| WO | WO 2009/066106 | 5/2009 |
| WO | WO 2012/022484 | 2/2012 |
| WO | WO 2013/140255 | 9/2013 |

OTHER PUBLICATIONS

U.S. Appl. No. 60/573,655, filed May 21, 2004, Richard Scott Weston.
U.S. Appl. No. 10/599,720, filed Oct. 6, 2006, Blott et al.
U.S. Appl. No. 12/192,000, filed Aug. 14, 2008, Hartwell et al.
U.S. Appl. No. 13/287,897, filed Nov. 2, 2011, Adie et al.
U.S. Appl. No. 13/287,959, filed Nov. 2, 2011, Adie et al.
Achterberg, V., Ph.D., Hydroactive dressings and serum proteins: an in vitro study, Journal of Wound Care, February, vol. 5, No. 2, 1996 (pp. 79-82).
Argenta, Louis C., et al., "Vacuum-Assisted Closure: A New Method for Wound Control and Treatment; Clinical Experience", Ann Plas Surg 1997;38:563-577 (Dec. 10, 1996).
Aubrey, D.A., et al., Treatment of the Perineal Wound after Proctectomy by Intermittent Irrigation, Arch. Surg., Oct. 1984, 119, 1141-1144.
Bagautdinov, N.A., "Variant of External Vacuum Aspiration in the Treatment of Purulent Diseases of Soft Tissues," in current Problems in Modern Clinical Surgery: Interdepartmental Collection, edited by V. Ye. Volkov et al. (Chuvashia State University, Cheboksary, USSR 1986) pp. 94-96 (with English translation).
Biblehimer, Helen L., "Dealing With a Wound that Drains 1.5 Liters a Day," RN, Aug. 1986, pp. 21-23, USA.
Bier, A., Hyperemia as a Therapeutic Agent, *Ed. Dr. Gustavus M. Blech, A. Robertson & Co.*, Chicago 1905, pp. 74-85.
Brubacher, "To Heal a Draining Wound", RN Mar. 1982, 7 pages.
Bucalo et al. "Inhibition of Cell Proliferation by Chronic Wound Fluid." Wound Repair and Regeneration, Miami, 1993, pp. 181-186.
Canadian Office Action for Canadian Application No. 2739605 dated Aug. 22, 2011 in 2 pages.
Chariker, M.E., et al, "Effective Management of Incisional and Cutaneous Fistulae with Closed Suction Wound Drainage," Contemporary Surgery. Jun. 1989, pp. 59-63, vol. 34 USA.
Chinese Office Action dated Aug. 29, 2008 for Patent Application No. 200480032101.1.
Chintamani, et al., "Half versus full vacuum suction drainage after modified radical mastectomy for breast cancer—a prospective randomized clinical trial", Research Article (Jan. 27, 2005), 1-5.
Costunchenok, BM, Effect of Vacuum on Surgical Purulent Wounds, Vestnik Chirurgia, 1986, 6 pages.
Davydov et al. "Pathogenic Mechanisms of the Effect of Vacuum Therapy on the Course of the Wound Process" pp. 43-46 (Dec. 1990).
Davydov, Yu A., et al., "Concepts for Clinical Biological Management of the Wound Process in the Treatment of Purulent Wounds Using Vacuum Therapy", The Kremlin Papers: Perspectives in Wound Care, Russian Journal: Vestnik Khirurgii, BlueSky Publishing, La Costa, California (2004), 15-17.
Davydov, Yu A., et al., "The Bacteriological and Cytological Assessment of Vacuum Therapy of Purulent Wounds", The Kremlin Papers: Perspectives in Wound Care, Russian Journal: Vestnik Khirurgii, BlueSky Publishing, La Costa, California (2004), 11-14.
Davydov, Yu A., et al., "Vacuum Therapy in the Treatment of Purulent Lactation Mastitis", The Kremlin Papers: Perspectives in Wound Care, Russian Journal: Vestnik Khirurgii, BlueSky Publishing, La Costa, California (2004), 5-7.
De Lange, M.Y., et al., "Vacuum-Assisted Closure: Indications and Clinical Experience", Eur J Plast Surg (2000) 2;178-182 (Feb. 9, 2000).
Dilmaghani et al., "A Method for Closed Irrigation and Suction Therapy in Deep Wound Infections," Journal of Bone and Joint Surgery, 1969, vol. 51-A, No. 2, pp. 323-342.
EPO, Office Action for EP App. No. 04 791 592.1 dated Jun. 12, 2008.
EPO, Second European Office Action for EP App. No. 04 791 592.1 dated Feb. 10, 2011.
Fleischmann, Vacuum sealing: indication, technique, and results, European Journal of Orthopaedic Surgery & Traumatology (1995), pp. 37-40.
Fleischmann, W. Wund Forum Spezial. IHW '94. "Vakuumversiegelung zur Behandlung von Problemwuden" (with English translation: Vacuum Sealing for Treatment of Problematical Wounds).
Garcia-Rinaldi, R., et al., Improving the Efficiency of Wound Drainage Catheters, Amer. Journ. of Surg., Sep. 1975, pp. 130, 372-373.
Hartz, R.S., et al., Healing of the Perineal Wound, Arch. Surg., Apr. 1980, 115, 471-474.
Health Technology, Literature R., "Vacuum Assisted Closure Therapy for Wound Care", Health Technology Literature Review (Dec. 2004), 3-59.
International Preliminary Report for International Application No. PCT/GB/2004/004549, dated Dec. 20, 2005.
International Search Report for International Application No. PCT/GB/2004/004549, dated Feb. 21, 2005.
Japanese Office Action dated Aug. 25, 2009 for Patent Application No. 2006-537411.
Japanese Office Action dated Dec. 15, 2009 for Patent Application No. 2006-537411.
Japanese Office Action dated Jun. 22, 2010 for Patent Application No. 2006-537411.
Japanese Office Action dated Jan. 17, 2012 for Patent Application No. 2010-59188.
Jeter, K.F., et al, "Managing Draining Wounds and Fistulae: New and Established Methods", Chronic Wound Care, pp. 240-246.
Johnson, F.E., An Improved Technique for Skin Graft Placement using a Suction Drain, Surgery, Gynecology and Obstetrics, Dec. 1984, 3 pages.
KCI Inc., If Its Not VAC Therapy, It's Not Negative Pressure Wound Therapy, Jan. 2005.
Khirugii, Vestnik, "A Collection of Published Studies Complementing the Research and Innovation of Wound Care", The Kremlin Papers, Perspectives in Wound Care, Russian Medical Journal, Vestnik Khirugii, Blue Sky Publishing (2004), 2-17.
Kostiuchenok, B. M., et al., "The Vacuum Effect in the Surgical Treatment of Purulent Wounds", The Kremlin Papers: Perspectives in Wound Care, Russian Journal: Vestnik Khirurgii, BlueSky Publishing, La Costa, California (2004), 3-4.
Landes, R.R. and I. Melnick, An Improved Suction Device for Draining Wounds, Arch. Surg., May 1972, 104, p. 707.
Linden, Willem van der, et al, "Randomized Trial of Drainage After Cholecystectomy: Suction Versus Static Drainage Through a Main Wound Versus a Stab Incision", American Journal of Surgery, Feb. 1981, vol. 141, pp. 289-294.
Mcfarlane, R.M., The Use of Continuous Suction under Skin Flaps, Br. Journ. Plast. Surg., pp. 77-86.
Mclaughlan, J, et al, "Sterile Microenvironment for Postoperative Wound Care", The Lancet, Sep. 2, 1978, pp. 503-504.
Meyer, W. and V. Schmeiden, Bier's Hyperemic Treatment, Published 1908 W. B. Saunders Company, pp. 44-65.
Morykwas, Michael J., et al., "Vacuum-Assisted Closure: A New Method for Wound Control and Treatment: Animal Studies and Basic Foundation", Ann Plast Surg 1997;38:553-562 (Dec. 10, 1996).

(56) References Cited

OTHER PUBLICATIONS

Nakayama, Y, et al, "A New Method for the Dressing of Free Skin Grafts", Plastic and Reconstructive Surgery, Dec. 1990 pp. 1216-1219, UK.
NURSING75, Wound Suction: Better Drainage with Fewer Problems, Nursing, vol. 5, No. 10, Oct. 1975, pp. 52-55.
Office Action (Final) for U.S. Appl. No. 10/575,875, published as 2007/129,707, dated Jun. 17, 2009 in 19 pages.
Ramirez, O.M., et al., Optimal Wound Healing under Op-Site Dressing, Ideas and Innovations, 73(3), pp. 474-475.
Ranson, J. H. C., et al, "Safer Intraperitoneal Sump Drainage", Surgery, Gynecology & Obstetrics, Nov. 1973, vol. 137, pp. 841-842.
Sames, C.P., Sealing of Wounds with Vacuum Drainage, Br. Med. Journ., Nov. 5, 1977, p. 1223, Correspondence.
Solovev, V. A., et al., "The Method of Treatment of Immature External Fistulas in the Upper Gastrointestinal Tract—Guidelines" USSR Ministry of Health, S. M. Kirov Gorky State Medical Institute, 1987 (with English translation).
Solovev, V.A. "Treatment and Prevention of Suture Failures after Gastric Resection" (Dissertation Abstract) (S.M. Kirov Gorky State Medical Institute, Gorky USSR 1988).
Stewart, Joanne, Ph.D., World Wide Wounds—Next generation of products for wound management—2002 (13 pages).
Svedman, P., "Irrigation Treatment in Split-Thickness Skin Grafting of Intractable Leg Ulcers," Scand J. Plast. Reconst. Surg., 19:211-213, 1985.
Svedman, P., "Irrigation Treatment of Leg Ulcers," The Lancet, Sep. 1983, 532-34.
Svedman, P., A Dressing Allowing Continuous Treatment of a Biosurface, IRCS Med. Science: Biomed. Tech.; Clinic. Med.; Surg. and Transplantation, 1979, 7, p. 221.
Svedman, P., et al., "A Dressing System Providing Fluid Supply and Suction Drainage Used for Continuous or Intermittent irrigation," Annals of Plastic Surgery, vol. 17, No. 2, Aug. 1986, pp. 125-133.
Swift, et al, "Quorum Sensing in *Aeromonas hydrophila* and *Aeromonas salmoncida*: Identification of LuxRl Homologs AhyRl and AsaRl and Their Cognate N-Acylhomoserine Lactone Signal Molecules," J. Bacteriol., 179(17):5271-5281 (1997).
Teder and Svedman et al., "Continuous Wound Irrigation in the Pig," Journal of Investigative Surgery, 1990, vol. 3, pp. 399-407.
Tribble, David E. M.D., An Improved Sump Drain-Irrigation Device of Simple Construction, Archives of Surgery New York, pp. 511-513, 1972 vol. 105.
Usupov, Y. N., et al., "Active Wound Drainage", The Kremlin Papers: Perspectives in Wound Care, Russian Journal: Vestnik Khirurgii, BlueSky Publishing, La Costa, California (2004), 8-10.
Venturi, Mark L., "Mechanisms and Clinical Applications of the Vacuum-Assisted Closure (VAC) Device", Am J Clin Dermatol (2005) 693, 185-194; Review Article (2005), 185-194.
Vijanto, J. and J. Raekallio, Local Hyperalimentation of Open Wounds, Br. J. surg., 1976, 63, 427-430.
Wackenfors, A., et al., Effects of Vacuum-Assisted Closure Therapy on Inguinal Wound Edge Microvascular Blood Flow, *Wound Rep. Reg, 2004, 12, 600-606.*
Webb, New Techniques in Wound Management: Vacuum-Assisted Wound Closure, Journal of the American Academy of Orthopaedic Surgeons, v. 10, No. 5, pp. 303-311, Sep. 2002.
Webster's Revised Unabridged Dictionary, published 1913 by C. & G. Merriam Co., definition of Flapper Valve, downloaded from Free Online Dictionary.
Wooding-Scott, Margaret, et al., "No Wound is Too Big for Resourceful Nurses," RN Dec. 1988, pp. 22-25 USA.
Wound Suction, Nursing, Oct. 1975, USA pp. 52-53.
Wu, W.S., et al. Vacuum therapy as an intermediate phase in would closure: a clinical experience, Eur J Plast Surg (2000) 23: pp. 174-177.
Search Report Dated Jan. 20, 2012 for PCT Appl. No. PCT/US2011/053707.
Westaby, S., et al., "A Wound Irrigation Device", The Lancet, Sep. 2, 1978, pp. 503-504.
US 6,306,115, 10/2001, Kelly et al. (withdrawn)

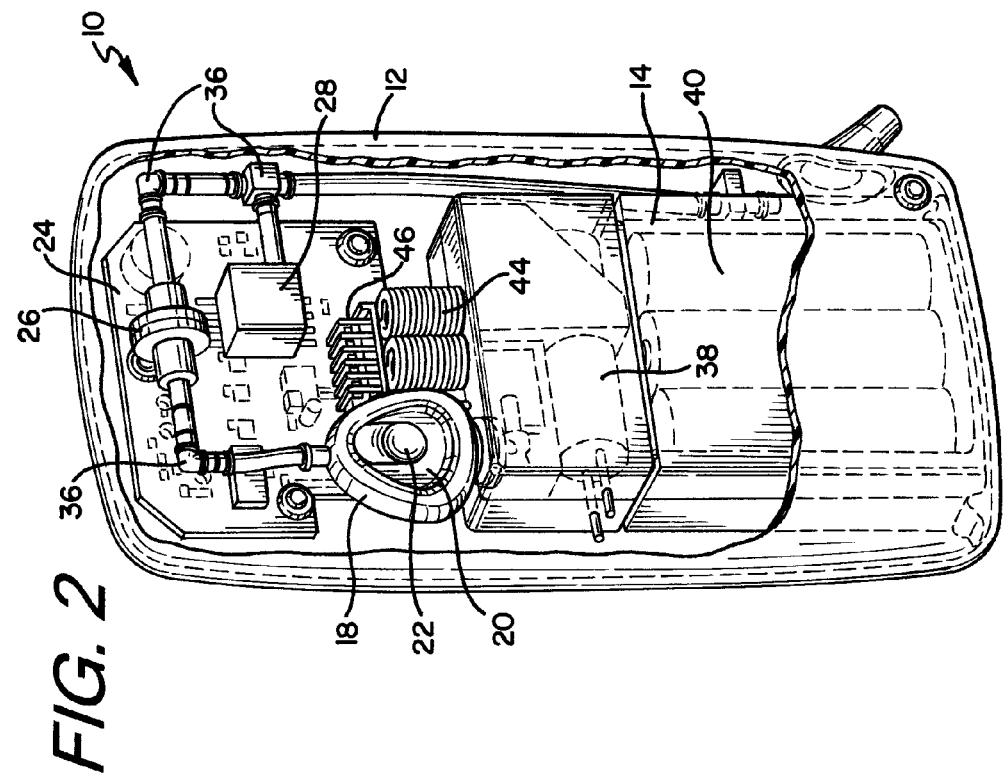
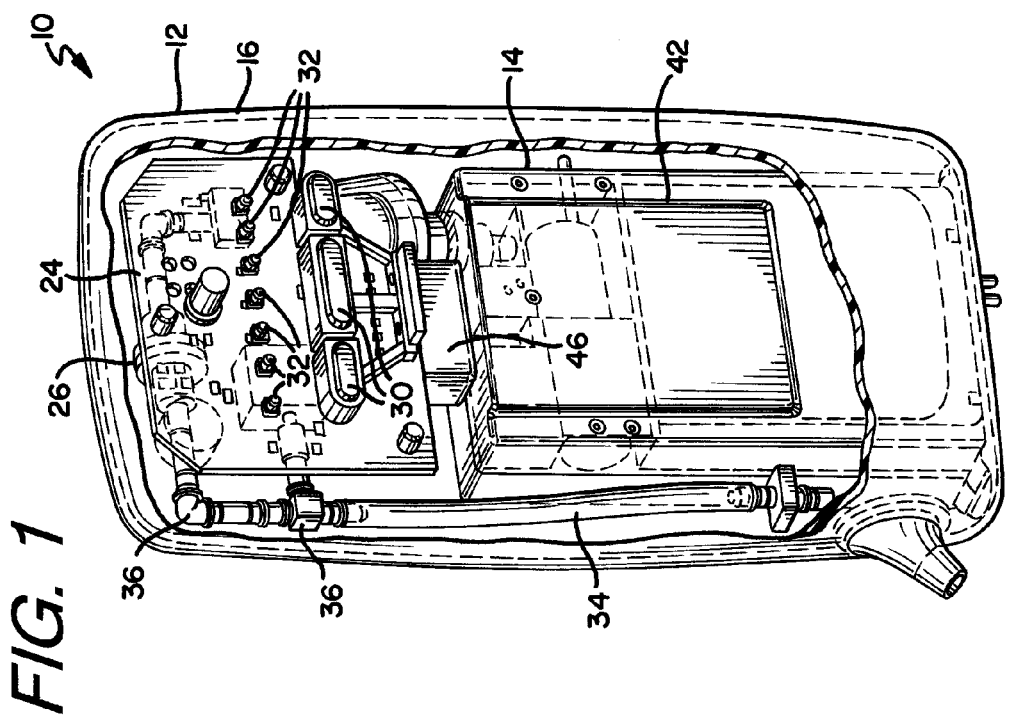

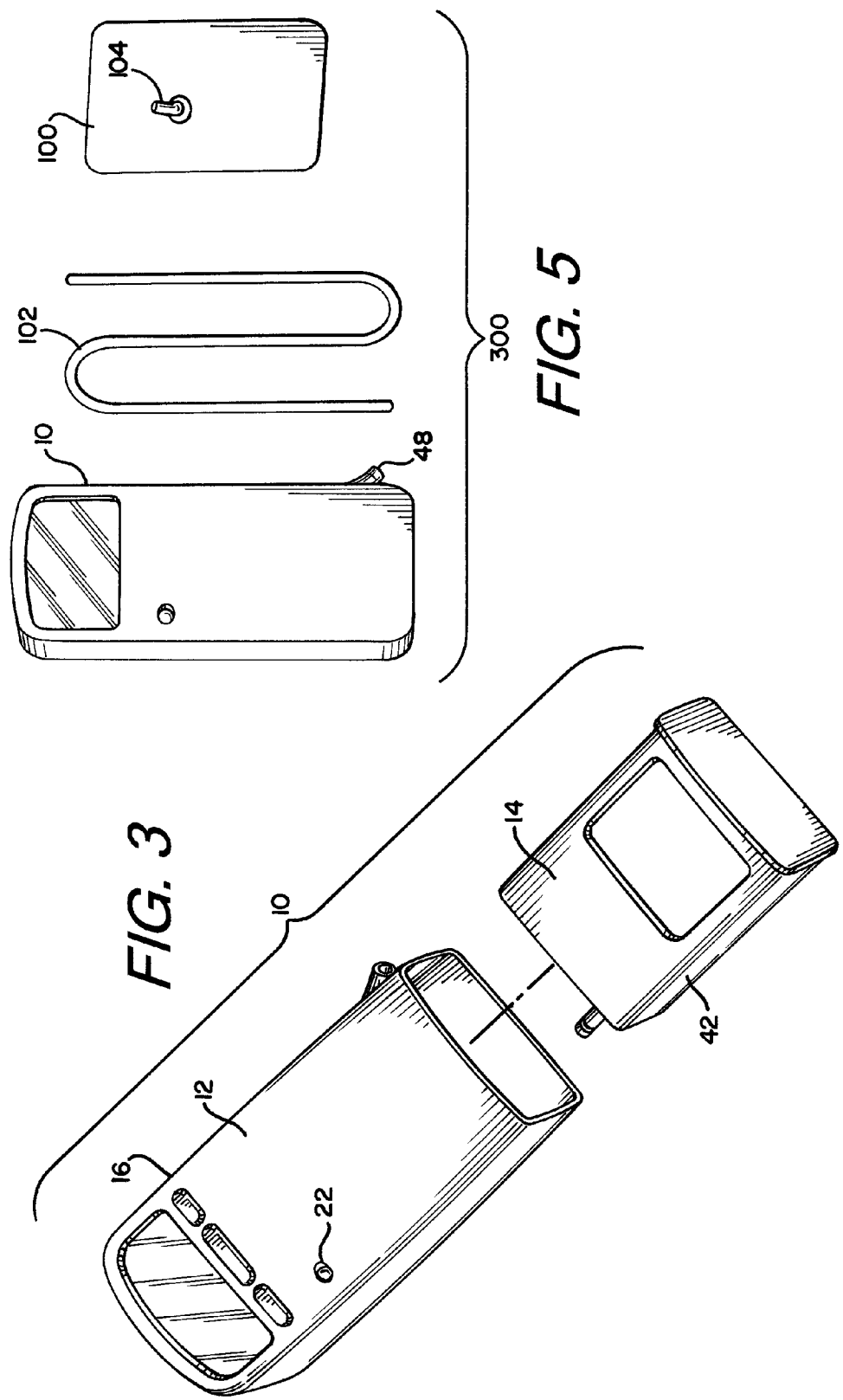

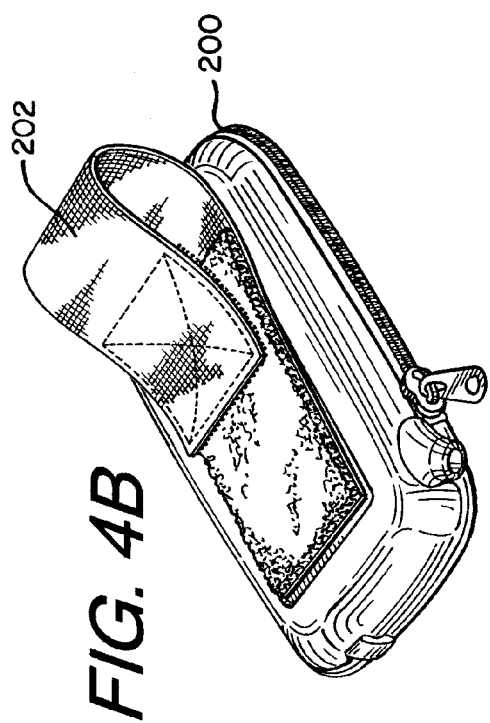
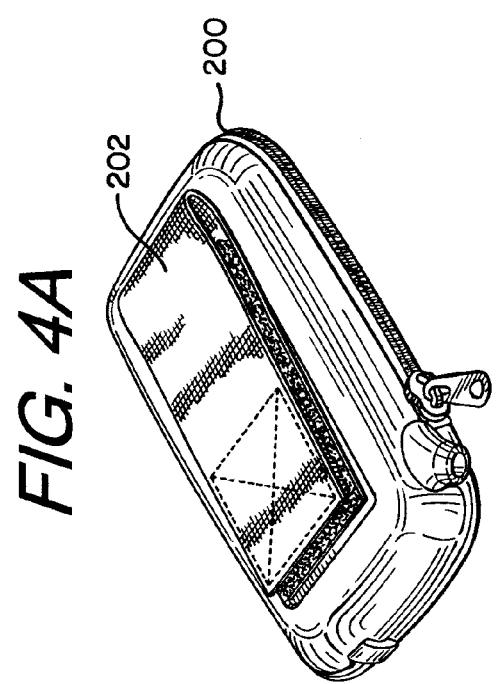
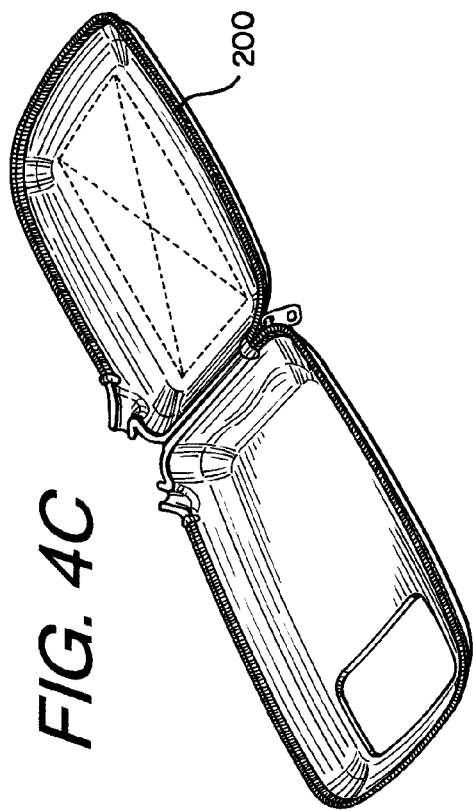

DEVICE WITH CONTROLLER AND PUMP MODULES FOR PROVIDING NEGATIVE PRESSURE FOR WOUND THERAPY

CROSS REFERENCE TO RELATED APPLICATIONS

This application claims priority to U.S. Provisional Application No. 61/489,299 filed on May 24, 2011, the entirety of which is incorporated herein.

FIELD OF THE INVENTION

The invention relates to a device having a controller module and pump module for providing negative pressure to a wound site.

BACKGROUND OF THE INVENTION

Negative pressure wound therapy is one method that is used to treat certain wounds or sores on people. In general, a bandage is placed over a wound site, and connected to a pump. The pump provides suction, creating a negative pressure under the bandage at the wound site. Exudates and other materials are removed from the wound site, and the wound healing progresses.

Some negative pressure wound therapy systems utilize large pumps because they require a canister, or other structure for storing exudates and other liquids removed from the wound site. Such systems can inhibit or interfere with a patient's movement during treatment and are generally large and cumbersome. Moreover, a patient can feel uncomfortable moving around with such a large pump and/or device being associated with his/her body.

On the other hand, there are certain negative pressure wound therapy systems that do not require such canisters as the exudates and other materials are stored within the disposable bandage. One such system/bandage is made available by Kalypto Medical, LLC. of Mendota Heights, Minn.

Since the device/system does not require a canister, a handheld pump (or other generally smaller pump) may be used in association with these types of bandages. For example, U.S. Pat. Pub. No. 2009/0299306 (assigned to the present applicant and the entirety of which is incorporated herein by reference) discloses a small pump that is used in association with such a bandage (that collects and stores liquids/exudates within the bandage). The pump disclosed therein utilities a controller module and a small pump in a pump module.

However, while such a device is beneficial and has significant advantages over the prior art systems and devices, it would be beneficial to minimize the components of the pump module, as it is believed that the pump is the structure most likely to fail in the device and require replacing and/or become contaminated requiring disposal of same.

Furthermore, it would be beneficial to minimize the time associated with switching out the pump module should a failure occur.

Finally, it would also be beneficial to minimize the amount of time needed for a clinician or practitioner to check on the status of the device.

The present invention is directed to resolving these and other matters.

SUMMARY OF THE INVENTION

In one embodiment of the invention, the invention is directed towards a device for use with a negative pressure wound therapy bandage, the device having a controller module which includes a housing, a circuit board having a CPU and support electronics, a check valve, and, a pressure sensor. The device also includes a pump module including a pump and a power source. The pump module is preferably removably contained in the housing.

As used herein, "module" refers to a selection of components contained within, for example, a housing and configured to be connected with one or more other modules to create a fully functioning device. Moreover, as described herein, when the pump module is described as containing the pump (preferably, for example in a second housing), it is meant that the entire pump is contained within the pump module (or housing). This is in contrast to those prior art systems wherein a pump head is separated from the pump driving element, and each are contained within separate modules (or housings).

A device according to this and other embodiments of the invention is believed to provide numerous benefits.

First, such a device minimizes the amount of materials and components within the pump module. As previously stated, it is believed that the pump is the most likely structure to fail and/or become contaminated. Thus, such a device will allow for a new pump module to be inserted into the device when necessary, without having to dispose of the entire device.

Further, the disclosed pump module minimizes the amount of waste, particularly e-waste, by removing most of the electronics and other components from the pump module and disposing them in the controller module which can be reused while the pump module can be disposed.

Moreover, such a device provides substantial financial benefits as a company (e.g, a hospital, care center, nursing home, medical supplier, etc.) can maintain a large supply of pump modules compared with a small supply of controller modules. The pump modules can be disposed of easily, while the controller module is reused with a different patient, or for a different negative pressure wound therapy treatment. Thus, each failure and/or contamination of a pump does not require disposal of the entire device, and the loss of the investment associated with same.

Furthermore, in devices where the pump is separated into a pump head and pump driving elements, a satisfactory seal is required between the two pieces of the pump. A device such as described herein, does not require this additional type of seal to be formed in the pump each time the modules are connected. This eliminates the chances of this seal failing, becoming comprised, or otherwise requiring a user to confirm that a full seal has been made each time the pump head is replaced.

In another embodiment of the invention, the invention is directed to a device for use with a negative pressure wound therapy bandage, the device having a controller module, a pump module, and, a connector for connecting the controller module to the pump module, wherein the connector provides a physical connection and a pneumatic connection. It is preferred that the connector is a push button/quick release connector that is easily accessible in the controller module (i.e., partially exposed).

In this embodiment, the controller module and pump module may have the same configurations as discussed above. Alternatively, they may have different configurations.

A device according to this and other embodiments of the invention is also believed to provide numerous other benefits.

Such a device would minimize the amount of time and effort needed to change out the pump module from the controller module. Rather than taking apart the controller module, or removing screws, one need simply depress the connector (in the case of a push button/quick release type connector) to remove the pump module.

The quicker and easier removal of the pump module minimizes the amount of time needed to switch the pump module, and, thus, minimizes the amount of time that changing the module can interfere with the negative pressure wound therapy treatment.

In still another embodiment of the invention, the invention is directed to a device for use with a negative pressure wound therapy bandage, the device having a controller module including a housing and a visual indicator and a pump module. The visual indicator provides an indication of a status of the device at a distance greater than 5 feet, preferably 10-15 feet.

In this embodiment of the invention, the controller module and the pump module may include the configurations discussed above. Further, this embodiment may also include the connection discussed above.

A device according to this and other embodiments of the invention is also believed to provide numerous benefits.

Specifically, allowing for the visual indicator to indicate status to a person at least five feet away would save time and energy for an observer, such as a nurse in a nursing home or hospital, where the observer must check multiple devices in multiple rooms. Such a device will allow the observer to simply look in to each patient's room to determine the status of the device therein. Over many rooms with many patients, the time savings can add up to a substantial savings for the observer. Further, while an audible alarm could perform the same task, it is not desired to use such an indicator in an environment where noises can be distracting and interfere with patients and/or other people (for example, where patients are sleeping, have roommates, or where the noise would other wise disrupt and become a distraction).

One or more embodiments of the device may be disposed in a carrying case including a strap. The carrying case may be disposable to promote cleanliness. Moreover, the strap will allow the case, and thus the device, to be mounted, for example, on a bed, a wheelchair, or an IV stand. It is contemplated that the strap is adjustable so that the case may also be mounted on a patient's body (for example the belt) to allow the patient freedom to move around, and minimize the visual appearance of the device (which can create uncomfortable feelings for the patient).

A further embodiment of the present invention is directed towards a kit containing a device according to the present invention and a negative pressure wound therapy bandage. The kit may also include tubing to connect the device to the bandage. The bandage may, but is not necessarily required to, collect and store exudates within the bandage.

It is to be understood that the aspects and objects of the present invention described above may be combinable and that other advantages and aspects of the present invention will become apparent upon reading the following description of the drawings and detailed description of the invention.

BRIEF DESCRIPTION OF THE DRAWINGS

The present invention will become more fully apparent from the following description and appended claims, taken in conjunction with the accompanying drawings. Understanding that the accompanying drawings depict only typical embodiments, and are, therefore, not to be considered to be limiting of the scope of the present disclosure, the embodiments will be described and explained with specificity and detail in reference to the accompanying drawings as provided below.

FIG. 1 is a front schematic view of a device according to one or more embodiments of the present invention.

FIG. 2 is a back schematic view of a device according to one or more embodiments of the present invention.

FIG. 3 is a perspective exploded view of a device according to one or more embodiments of the present invention.

FIG. 4a is a case for use with a device according to the present invention with a strap in a first configuration.

FIG. 4b is a case for use with a device according to the present invention with a strap in a second configuration.

FIG. 4c is a case for use with a device according to the present invention.

FIG. 5 is a kit according to the present invention.

DETAILED DESCRIPTION OF THE DRAWINGS

While this invention is susceptible of embodiment in many different forms, there is shown in the drawings and will herein be described in detail one or more embodiments with the understanding that the present disclosure is to be considered as an exemplification of the principles of the invention and is not intended to limit the invention to the embodiments illustrated.

Reference throughout this description to features, advantages, objects or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

As shown in the attached drawings, the present invention is directed towards a device 10 having a controller module 12 and a pump module 14.

The pump module 14 is preferably removably contained within the controller module 12 and more specifically within a housing 16 of the controller module 12, and most preferably slidably received in the housing 16.

In certain embodiments of the present invention, the device 10 includes a connector 18 which provides both a physical connection and a pneumatic connection. The physical connection functions to hold the pump module 14 in place. The pneumatic connection functions to allow for the communication of negative pressure from the device 10 to a negative pressure wound therapy bandage 100.

The connector 18 may include an interference fit, a snap fit, a friction fit, and any other connecting mechanism and structure so long as the connector 18 provide the necessary physical and pneumatic connection, while at the same time allowing for a relatively quick disconnection.

It is preferred that the connector 18 is partially exposed in the housing 16 so that it may be easily accessible. In a most preferred embodiment, the connector 18 is a quick release connector—wherein the connector 18 includes a button 20 disposed inside of the housing 16 of the controller module 12 that may be only partially exposed through an aperture 22 in the housing 16 of the controller module 12.

The controller module 12 may also include a circuit board 24 with a CPU and other support electronics, a check valve 26 and a pressure sensor 28—preferably all contained within the housing 16. The check valve 26 aides in maintaining pressure at the wound site. The pressure sensor 28 determines the negative pressure begin communicated to the wound site.

The controller module 12 may also include buttons 30 for allowing interaction and control of the device 10. For example the device 10 may be provided with three buttons 26: one for power; one to select and adjust settings; and, one to lock the device 10.

Further, in some embodiments of the present invention, the controller module 12 may also include one or more visual indicators 32, such as LEDs, through holes LEDs with a lens, other lighted icons/backlit LEDS, or other lights to indicate the status of the device 10. Preferably the visual indicator(s) 28 provide the status at a distance greater than 5 feet, preferably between 10-15 feet. This would allow the device 10 to provide indications to a clinician or other practitioner, for example, without requiring same to walk up to the device 10. The indicated status may include "off," "on," "pump mode on," "leak detection," "low battery detection," "unknown error detection," or any other status that may be considered relevant to provide relative to the use of the device 10 in providing negative pressure wound therapy.

Finally, the controller module 12 may also preferably contain tubes 34, pipes and joints 36 for communicating negative pressure from the device 10 to the appropriate structures (check valve 26, pressure sensor 28) of the controller module 12 and ultimately to a negative pressure wound therapy bandage 100.

Turning to the pump module 14, the pump module 14 may contain the pump 38 and a power source 40. The pump 38 provides the negative pressure used in the negative pressure wound therapy treatment. It is preferred that the device 10 is portable and does not require power from an outlet, and thus, the power source 40 may be batteries, for example, 3 AA batteries.

These structures of the pump module 14, as well as others, may be contained in a housing 42 of the pump module 14. The housing 42 is preferably received by the housing 16 of the controller module 12. Moreover, as mentioned, the pump module 14/housing 42 may be retained in the housing 16 of the controller module 12 with a connector 18.

One or more springs 44 may be positioned within the controller module 12 to aid in the removal of the pump module 14. As shown, the springs 44 may be configured such that they provide a force to move the pump module 14 out of the housing 16 of the controller module 12 such that if the connector 18 is disengaged, the pump module 14 is pushed out of the housing 16 of the controller module 12.

Further, both the pump module 14 and the controller module 12 may have complementary configured electrical connectors 46 for transmitting power from the power source 40 to the controller module 12, as well as to allow for communication between the pump 38 and CPU/electronics 24 in the controller module 12. For example, a 12 pin PCB connector may be utilized.

In this manner, negative pressure is created by the pump 38 and communicated through the connector 18 to the controller module 12. In the controller module 12, the negative pressure is communicated through a check valve 26 and a pressure sensor 28, via the pipes and joints 36. Finally, the negative pressure is communicated out of the controller module 12 (and device 10), for example, through a port 48, to a negative pressure wound therapy bandage 100.

It is contemplated that the device 10 is placed in case 200. See, FIGS. 4a-4c. Since the device 10 is intended to be used with multiple patients, albeit at different times, it is preferred that the case 200 be disposed of between patients. The case 200 may include a strap 202 to mount the device 10. The strap 202 may be adjustable to allow for the case and device to be mounted on a variety of different things, such as a belt, a bed, a wheelchair, an IV pole, etc. For example, during the day, the device 10 can be worn by a patient on a belt. Later in the evening, it can be mounted on a bed. If it is mounted on a bed, it is preferred that the device 10 include the visual indicator(s) 32 so that a practitioner or clinician need only see the device 10 from a distance to know its status.

Finally, it is further contemplated that the device 10 is provided in a kit 300 containing a negative pressure wound therapy bandage 100. Preferably the kit 300 includes tubing 102 to connect the device 10 (preferably through port 48) to, for example, a second port 104 on the bandage 100.

While various embodiments of the present invention have been described as used in association with a negative pressure wound therapy bandage that collects and stores exudates within the bandage, it will be appreciated by one of ordinary skill in the art that the embodiments of the present invention, if desired, can be used with an external collection device and a bandage that does not collect and store exudates in the bandage by utilizing a collection device (canister, flask, etc.) and additional tubing with connectors.

As discussed above, a device according to one or more embodiments of the present invention is believed to provide a number of advantageous and benefits in the field of providing negative pressure wound therapy.

It is to be understood that additional embodiments of the present invention described herein may be contemplated by one of ordinary skill in the art and that the scope of the present invention is not limited to the embodiments disclosed. While specific embodiments of the present invention have been illustrated and described, numerous modifications come to mind without significantly departing from the spirit of the invention, and the scope of protection is only limited by the scope of the accompanying claims.

What is claimed is:

1. A device for use with a negative pressure wound therapy bandage, the device comprising:
    a controller module including:
        a housing configured to receive a pump module and configured to substantially enclose the pump module;
        a circuit board having a CPU and support electronics;
        a check valve; and,
        a pressure sensor; and
    the pump module including a pump and a power source, the pump module configured to be placed in the housing recess and to be removably enclosed by the housing,
    wherein negative pressure from the pump is communicated through at least the check valve to the negative pressure wound therapy bandage.

2. A kit comprising:
    a device including:
        a controller module including:
            a housing configured to receive a pump module and configured to substantially enclose the pump module,
            a circuit board having a CPU and support electronics,
            a check valve, and,
            a pressure sensor; and,
        the pump module including a pump and a power source, the pump module configured to be placed in the housing and to be removably enclosed by the housing;
    a negative pressure wound therapy bandage,
    wherein negative pressure from the pump is communicated through at least the check valve to the negative pressure wound therapy bandage.

3. The device of claim 1 wherein the pump module includes a housing and the pump and power source are contained within the housing of the pump module.

4. The device of claim 3 wherein the housing of the controller module slidably receives the housing of the pump module.

5. The device of claim 1 further comprising:
a connector for connecting the controller module to the pump module, wherein the connector provides a physical connection and a pneumatic connection.

6. The device of claim 5 wherein the connector includes a button release.

7. The device of claim 6 wherein the housing of the controller module includes an aperture and the button release is accessible through the aperture.

8. The device of claim 1 wherein the pump creates a negative pressure that is communicated to the controller module and out of the controller module though a port in the housing of the controller module.

9. The device of claim 1 wherein the controller module further includes at least one visual indicator that provides an indication of a status of the device at a distance greater than 5 feet.

10. The device of claim 9 further comprising a case removably receiving the device and having an adjustable strap capable of being mounted on a plurality of different items.

11. The device of claim 1 further comprising at least one spring in the housing of the controller module that provides a force on the pump module away from the controller module.

12. The device of claim 5 further comprising at least one spring in the housing of the controller module wherein when the connector is disengaged the at least one spring provides a force on the pump module to move the mump module away from the controller module.

13. The kit of claim 2 further comprising:
a connector for connecting the controller module to the pump module, wherein the connector provides a physical connection and a pneumatic connection.

14. The kit of claim 2 wherein the negative pressure wound therapy bandage collects and stores exudates within the bandage.

15. The kit of claim 2 further comprising tubing to connect the device to the negative pressure wound therapy bandage.

16. The device of claim 1 further comprising tubing to connect the device to the negative pressure wound therapy bandage.

17. The kit of claim 13 wherein the connector includes a button release.

18. The kit of claim 17 wherein the housing of the controller module includes an aperture and the button release is accessible through the aperture.

* * * * *

UNITED STATES PATENT AND TRADEMARK OFFICE
CERTIFICATE OF CORRECTION

| | | |
|---|---|---|
| PATENT NO. | : 8,945,074 B2 | Page 1 of 1 |
| APPLICATION NO. | : 13/247435 | |
| DATED | : February 3, 2015 | |
| INVENTOR(S) | : John Buan | |

It is certified that error appears in the above-identified patent and that said Letters Patent is hereby corrected as shown below:

Title Page,

In column 1 (page 5, item 56) at line 34, Under Other Publications, change "Plas" to --Plast--.

In column 2 (page 5, item 56) at line 20, Under Other Publications, change "Problemwuden"" to --Problemwunden"--.

In column 2 (page 6, item 56) at line 2, Under Other Publications, change "salmoncida:" to --salmonicida:--.

In the Specification,

In column 3 at line 34, Change "other wise" to --otherwise--.

In column 5 at line 9, Change "LEDS," to --LEDs,--.

In the Claims,

In column 8 at line 4, In Claim 12, change "mump" to --pump--.

Signed and Sealed this
Twenty-seventh Day of October, 2015

Michelle K. Lee
*Director of the United States Patent and Trademark Office*